(12) United States Patent
Shakespeare et al.

(10) Patent No.: US 8,212,222 B2
(45) Date of Patent: Jul. 3, 2012

(54) SPA CHLORINE MEASUREMENT VIA TEMPERATURE SHIFT UV SPECTROMETRY

(75) Inventors: Simon Adam Shakespeare, Atherstone (GB); Matthew Emmanuel Milton Storkey, Trumpington (GB)

(73) Assignee: Watkins Manufacturing Corporation, Vista, CA (US)

( * ) Notice: Subject to any disclaimer, the term of this patent is extended or adjusted under 35 U.S.C. 154(b) by 479 days.

(21) Appl. No.: 12/388,074

(22) Filed: Feb. 18, 2009

(65) Prior Publication Data

US 2009/0219513 A1 Sep. 3, 2009

Related U.S. Application Data

(60) Provisional application No. 61/032,346, filed on Feb. 28, 2008.

(51) Int. Cl.
*G01N 21/72* (2006.01)
(52) U.S. Cl. ....................................................... 250/373
(58) Field of Classification Search .................... 250/373
See application file for complete search history.

(56) References Cited

U.S. PATENT DOCUMENTS

| | | | |
|---|---|---|---|
| 3,306,156 A | | 2/1967 | Glasser et al. |
| 3,565,252 A | * | 2/1971 | Sheehy et al. ................ 210/104 |
| 3,751,173 A | * | 8/1973 | Sanz et al. ................... 356/246 |
| 4,311,485 A | * | 1/1982 | Saltzman et al. ............. 436/101 |
| 5,300,442 A | | 4/1994 | Frant |
| 6,831,746 B2 | * | 12/2004 | Cassidy et al. ............... 356/437 |

FOREIGN PATENT DOCUMENTS

WO WO 97-42497 A1 11/1997

OTHER PUBLICATIONS

M. Ralfs et al, Disposable optochemical sensor for the determination of chlorine concentrations in the ppf-range, Sensors and Actuators B, 1997, vol. 44, pp. 257-261.
Makoto Mizoguchi et al., A Novel Method to Determine Chlorine Concentration in Tap Water Using a New Tolidine Derivative with less Cytotoxicity, Analytical Sciences, 2001, vol. 17 Supplemental, pp. i829-i831.
Watkins Manufacturing Corporation et al., Form PCT/ISA/210 in connection with PCT/US2009/034569.
Watkins Manufacturing Corporation et al., Form PCT/ISA/237 in connection with PCT/US2009/034569.

\* cited by examiner

*Primary Examiner* — David Porta
*Assistant Examiner* — Shun Lee
(74) *Attorney, Agent, or Firm* — Greenberg Traurig LLP; Franklin D. Ubell

(57) ABSTRACT

A method of measuring chlorine concentration of a solution comprising making a first measurement of transmission of ultraviolet light at a selected wavelength through a first sample of said solution at a first temperature; making a second measurement of the transmission of ultraviolet light at said selected wavelength through a second sample of said solution at a second temperature, said second temperature being different than said first temperature; and determining the chlorine concentration in said solution using the results of said first and second measurements.

11 Claims, 5 Drawing Sheets

SPA CHLORINE MEASUREMENT VIA TEMPERATURE SHIFT UV SPECTROMETRY

RELATED APPLICATIONS

This application claims the benefit of and priority to U.S. Provisional Application Ser. No. 61/032,346, filed Feb. 28, 2008, entitled, "Spa Chlorine Measurement Via Temperature Shift UV Spectrometry," the contents of which are incorporated by reference herein in its entirety.

BACKGROUND

The subject invention relates to halogen detection in fluid solutions and more particularly to a chlorine concentration detection system for analyzing chlorine concentration in water wherein the system employs UV spectral analysis of a solution at two different temperatures.

BRIEF DESCRIPTION OF THE DRAWINGS

The above-mentioned features and objects of the present disclosure will become more apparent with reference to the following description taken in conjunction with the accompanying drawings wherein like reference numerals denote like elements and in which.

SUMMARY

A chlorine concentration sensor, according to an illustrative embodiment, exploits the variability in the equilibrium point of HOCl/OCl$^-$ with temperature. By taking the difference (absolute difference or ratio) from a single wavelength, for example, at 293 nanometers (nm) (the absorption peak of the OCl$^-$ species) at two different temperatures, the level of OCl$^-$ can be determined. It has been determined experimentally that the absorption spectra of strongly ionised salts, such as nitrates and carbonates dissolved in solution, do not change with temperature and so do not affect the difference measurement.

A system according to an illustrative embodiment may include a spa or other water holding vessel, a filter and a pump. The pump circulates water through the filter and heater and back to the spa. The system may also include an ozone generator. In order to analyze chlorine level, water is sampled and passed to a subsystem including first and second bypass valves, a heat exchanger and a spectral analyzer including a cuvette, UV source and detector. Heated and unheated water samples are provided to the spectral analyzer and the absorption (transmission) spectrum of each sample is then measured and compared.

DETAILED DESCRIPTION

In the following detailed description of embodiments of the invention, reference is made to the accompanying drawings in which like references indicate similar elements, and in which is shown by way of illustration specific embodiments in which the invention may be practiced. These embodiments are described in sufficient detail to enable those skilled in the art to practice the invention, and it is to be understood that other embodiments may be utilized and that logical, mechanical, biological, electrical, functional, and other changes may be made without departing from the scope of the present invention. The following detailed description is, therefore, not to be taken in a limiting sense, and the scope of the present invention is defined only by the appended claims. As used in the present disclosure, the term "or" shall be understood to be defined as a logical disjunction and shall not indicate an exclusive disjunction unless expressly indicated as such or notated as "xor."

A chlorine concentration sensor, according to an illustrative embodiment, exploits the variability in the equilibrium point of a hydrochlorous acid/chlorous-ion (HOCl/OCl$^-$) and water solution with temperature or pH. By taking the difference (absolute difference or ratio) from a single wavelength at 293 nm (the absorption peak of the OCl$^-$ species) at two different temperatures, the level of OCl$^-$ can be determined. It has been determined experimentally that the absorption spectra of strongly ionized salts, such as nitrates and carbonates dissolved in solution, do not change with temperature and so do not affect the difference measurement.

Figure 1:
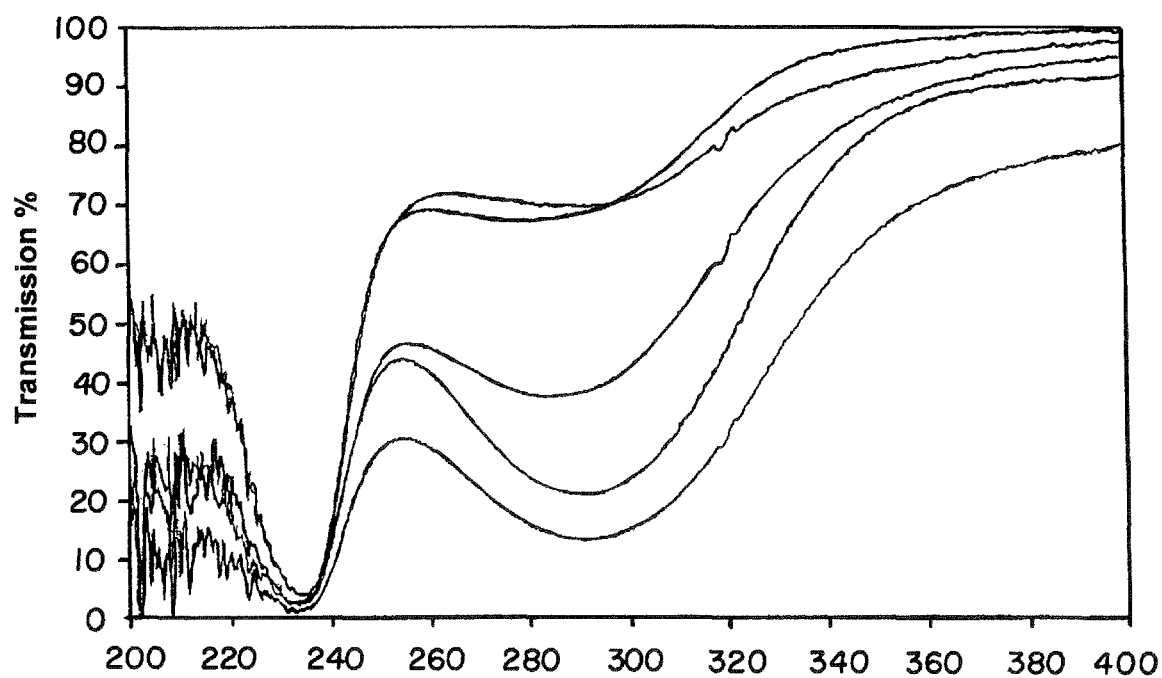
FIG. 1 is a spectral graph showing ultraviolet light transmission of three different solutions at different temperatures.

FIG. 1 shows a set of experiments used to show the transmission of UV for a range of concentrations of hypochlorite at different temperatures, with a constant pH of 7.5. With tap water containing no hypochlorite ions, there is almost no change of absorption over the whole range. From theory, the only species present in the water are strong salts such as sodium chloride, sodium carbonate, and ammonium nitrate. Strong salts such as these are fully dissociated in water and their concentration remains constant and independent of temperature.

With a concentration of hypochlorite of 2 ppm (at 25° C.), more light is absorbed at 293 nm at the higher temperature, 37.5° C. than at the lower temperature 25° C. From theory, the absorption peak at 293 nm is directly related to the concentration of the hypochlorite ion OCl$^-$ in solution. This result indicates that the level of hypochlorite in solution increases with temperature. Similarly, at a concentration of 6 ppm (at 25° C.), more UV is absorbed at the higher temperature.

Hypochlorous acid is a weak acid, which means that it exhibits only partial dissociation in solution, producing a hydrogen ion and a hypochlorite ion, as shown in Equation I:

$$HOCl \leftrightharpoons H^+ + OCl^-$$

Equation I—partial dissociation of hypochlorous acid

The equilibrium point of this dissociation is dependent on both the pH and the temperature.

Figure 2:
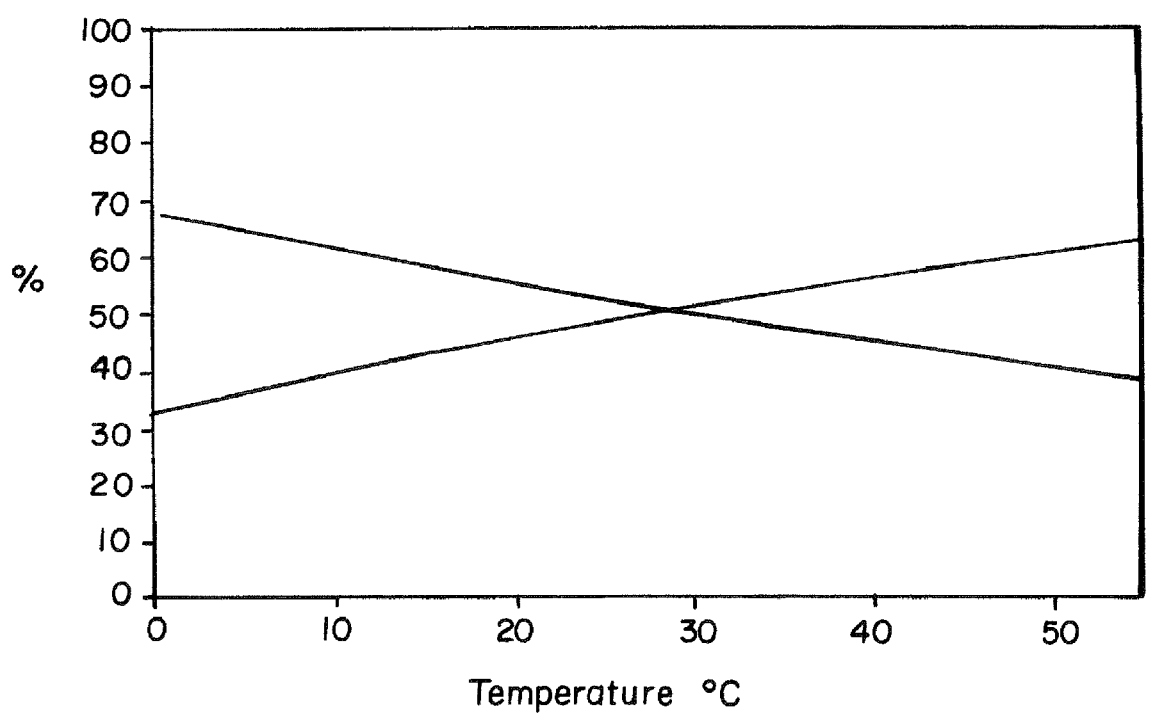
FIG. 2 is a graph illustrating the relative distribution of HOCl and OCl$^-$ ions in solution with temperature.

FIG. 2 illustrates the theoretical relationship between the relative concentrations of hypochlorous acid and hypochlorite ion with temperature. As shown, with increasing temperature the relative concentration of OCl$^-$ increases as the HOCl dissociates, moving the equilibrium point further to the right hand side of the equation.

The concentration of OCl$^-$ as predicted by the absorption of UV at 293 nm should be closely correlated to the concentration of OCl$^-$ as predicted by temperature. From this analysis, it can be seen that a change in temperature has the effect of changing the relative concentrations of HOCl and OCl$^-$ in solution by shifting the point of equilibrium. This change may be detected by looking at the change in absorption at 293 nm, where OCl$^-$ has its peak absorption.

Use of a heat controller allows stable and uniform sample temperatures to be maintained. Collection of data over a wider temperature range will also produce a more accurate relationship between the active sanitizer and the UV transmission spectra, with temperature.

Figure 3:
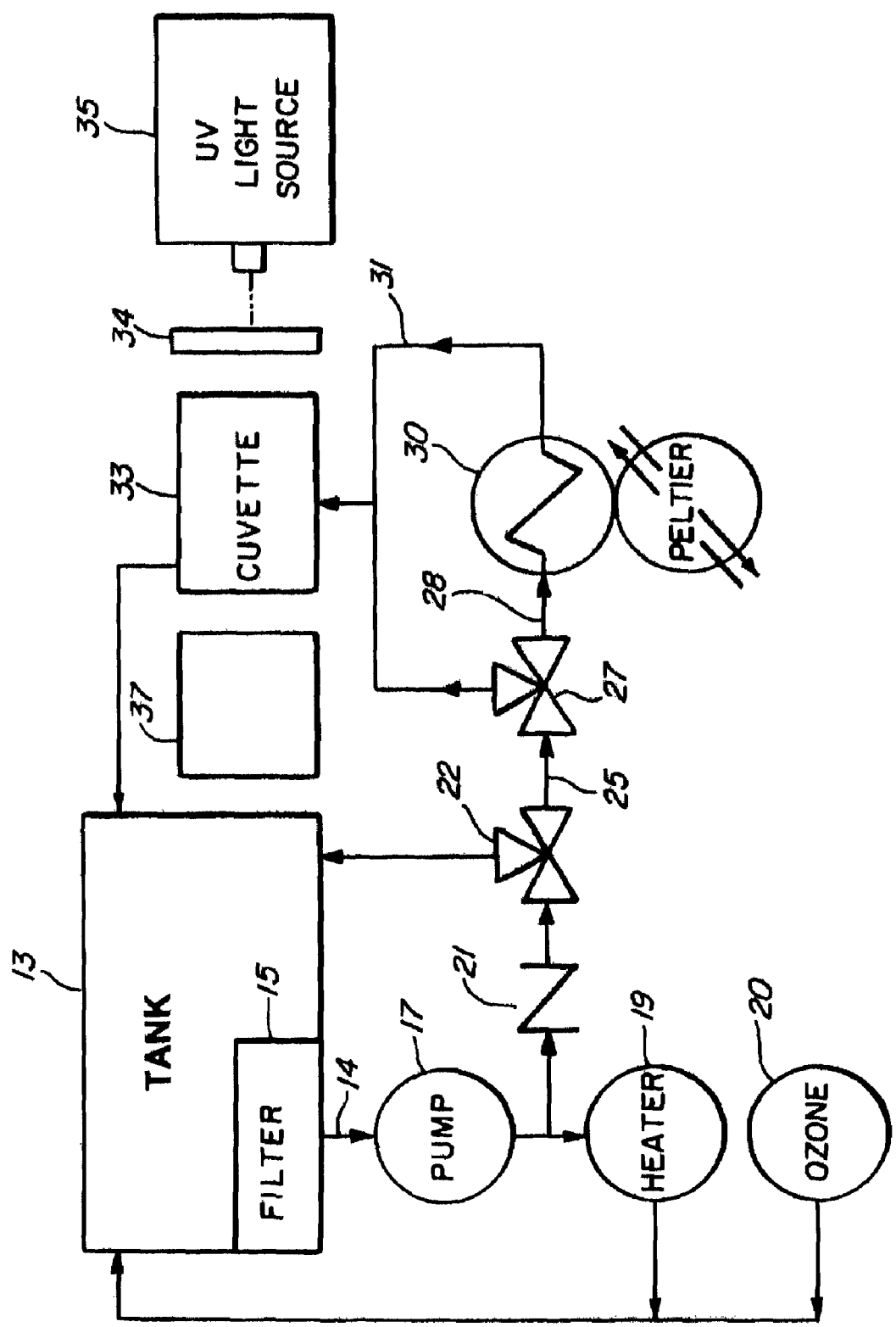
FIG. 3 is a schematic diagram of a system for chlorine concentration detection according to an illustrative embodiment.

FIG. 3 illustrates embodiments of a system including a chlorine concentration measuring apparatus. The system includes a spa or other water holding vessel 13, a filter 15, and a pump 17. The pump 17 circulates water through the filter 15 and heater 19 and back to the spa 13. The system may also include an ozone generator 20. In order to detect or analyze chlorine level, water is sampled via a valve 21 and passed to a subsystem including first and second bypass valves 22, 27 interconnected by a fluid transmission line 25, a heat exchanger 30 and a spectral analyzer including a cuvette 33, UV source 35, UV filter 34, and detector 37. A fluid transmission line 28 connects the valve 27 to the heat exchanger 30. The valves 22, 27 facilitate passing an unheated water sample to the cuvette 33 and thereafter passing a heated sample from the heat exchanger 30 through a fluid transmission line 31 to the cuvette 33 for analysis.

UV Source

In the illustrative embodiment, a UV source 35 emitting a wavelength of 293 nm is utilized, a wavelength bordering between UVC and UVB. Ultraviolet light with this wavelength can be obtained using a discharge tube filled with deuterium gas. However, such tubes are expensive and it would be preferable to use an UV LED, with an output at (or about) 293 nm. UV LEDs in this band are now being manufactured and can be purchased. For example, Sensor Electronic Technology manufactures UV LEDs with outputs between 255 nm and 365 nm, using a technology based on AlGaN/GaN.

Figure 4:
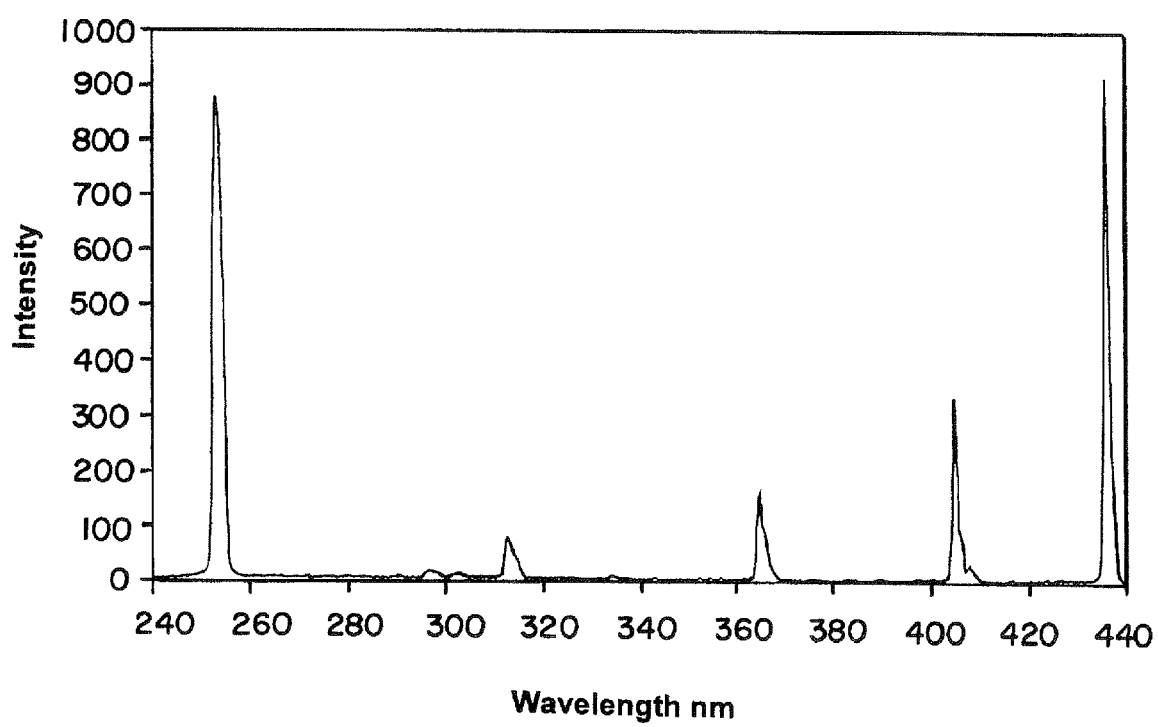
FIG. 4 is a graph illustrating the spectral output of a mercury discharge tube.
Figure 5:
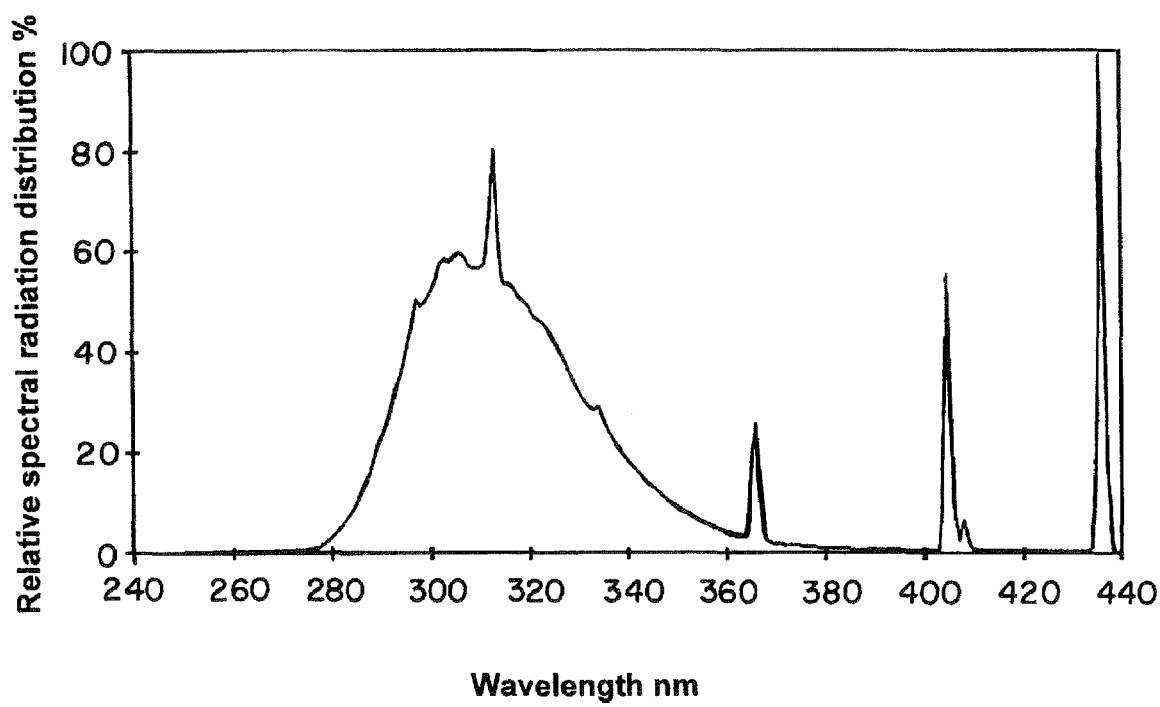
FIG. 5 is a graph illustrating the spectral output of a Waldman UVB tube.

Another alternative to obtain the desired 293 nm wavelength is to use a low cost mercury tube with a fluorescent material to shift the wavelength from 254 nm to 293 nm. FIG. 4 shows the spectral output of a standard fluorescent tube, and FIG. 5 shows the output when a phosphor coating is used to shift output at 254 nm into a broad output in the UVB band (280-340 nm).

Standard fluorescent 'phosphors' used in televisions and fluorescent lamps are based on rare earth materials such as strontium aluminate and other compounds that absorb UV and re-radiate in the visible. Although not widely used, there are compounds that absorb in the UVC and transmit at longer UVB wavelengths. Thus, a custom phosphor could be created that had a peak emission at 293 nm.

The most common applications that require a source of UVB radiation are sun-tanning beds, reptile terrariums and treatment of psoriasis. Some UVB sources are available off-the-shelf but there is only a small amount of UV from these tubes at 293 nm. Typical UVB bulbs from the largest fluorescent tube manufacturers, Philips and Sylvania, peak at 310 nm. These may find use in embodiments of the invention, as the chlorous ion has a broad absorption spectra, including 310 nm. Waldmann Medizintechnik GmbH (a German manufacturer that makes fluorescent tubes for medical phototherapy) makes a broad source of UVB with a range from 280-360 nm (See FIG. 5).

UV Filter

One of the many advantages of using LEDs is that they are essentially monochromatic, producing a single color (or at least, a very narrow frequency band). This is highly advantageous as in-line UV filters such as filter 34 would not be required-removing cost, optical complexity, and another light absorbing material in the optical path.

If a broad-band UV light source is to be used, then a UV band-pass filter 34 centred at 293 nm is used. Filter 34 may be a custom (and expensive) filter. A ruled grating also can be considered, but would require more complicated optics as a non-perpendicular light path is used. Dye filters are available at very low cost, but have a very broad band of transmission.

It may be possible to use a broad source of UVB, or a line close to the optimal wavelength of 293 nm. Again, such sources would be considered only if available UV LEDs have an insufficient light output. It is reasonable to assume that a broad UV source could be used, as the chlorous ion has a broad absorption across the UVB band. If this proves to be the case, a low cost broad passband dye filter may be appropriate for this application; otherwise a grating or interference filter may be used.

UV Transparent Cuvette

Cuvette 33 is low friction with UV transparent windows. The windows are self-cleaning and UV transparent. There are several polymer films (or polymer coatings) that can be used to serve this function, including the fluoropolymers FEP (e.g. Teflon®), PTFE and ETFE. A specific blend of the co-polymer Ethylene Tetrafluroethylene (ETFE), may meet these two necessary requirements. These plastics are manufactured by DuPont (under the trade name Tefzel®) and 3M (from the subsidiary Dyneonunder the trade name Hostaflon®). As the film is only available in thin films (typically 10-200 um), it may prove necessary to laminate the film onto a stronger substrate to increase rigidity. Another material that is UV transparent, for example quartz, may also be used to construct the cuvette 33.

The UV detector 37 is preferably based around a UV sensitive photodiode connected to follow-on amplification electronics, which may include a microcontroller to control taking the optical readings, perform any pre-processing and determine the chlorine concentration, for example, via a table look-up operation.

Water entering cuvette 33 should be uniform in temperature to obtain an accurate reading. The most expedient way to achieve this is by heating (or cooling) the water as it flows through the heat exchanger 30, preferably a copper heat exchanger, before the water enters the cuvette 33. Although it is possible to heat (or cool) the cuvette 33 directly, such direct heating is likely to produce large temperature gradients and non-uniform heating. The temperature control stage may include a closed loop controlled peltier device that can heat or cool the water entering the cuvette 33. Peltier controllers are available commercially off-the-shelf with an RS232 control interface.

It may be noted that many spas intentionally introduce ozone in the water, as a sanitizer and clarifier. Standards dictate that the residual level of ozone entering into the main body of the spa should be less than 0.1 ppm. The standard technique for measuring ozone dissolved in water is by using a UV spectrometer that examines the peak at 253.8 nm.

It is well known that ozone absorbs UV in the UVB and UVC bands and in air. At the concentrations suggested, however, ozone should not absorb UV to any significant degree. If ozone does present a difficulty when attempting to measure hypochlorite levels, the ozone may be turned off for a period before measurements are taken.

A system using the relationship for the dissociation of hypochlorous acid with temperature will need to ensure that other species in the spa water will not undergo a similar effect. As shown, strong salts in an unsaturated solution are fully dissociated and their concentration does not change with temperature. Other contaminants, such as beverages, suncreams and personal care produce may have a level of solubility/dissociation that is related to temperature. Pool scents, used for aromatherapy also are contaminants that are often added to spas, which may affect results.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. An apparatus comprising:
    a valve system configured to supply first and second samples of a solution successively to a single container, the first sample having a temperature which is different than that of the second sample; and
    a spectral analyzer configured to:
        make a first measurement of transmission of ultraviolet light at a selected wavelength through the first sample of the solution present in said container;
        make a second measurement of the transmission of ultraviolet light at said selected wavelength through the second sample of the solution present in said container; and
        determine a concentration of a halogen in the solution using the results of the first and the second measurements.

2. The apparatus of claim 1 further comprising:
    a spa filled with a liquid comprising water;
    a heater;
    a filter; and
    a pump for circulating the liquid through the heater and the filter and back to the spa; and
    wherein the valve system samples the liquid to produce said solution.

3. The apparatus of claim 2, wherein the valve system comprises first and second valves.

4. The apparatus of claim 2, wherein the selected wavelength is 293 nanometers.

5. The apparatus of claim 4 wherein said spectral analyzer is configured to determine the concentration of a halogen by determining the difference between the first and second measurements.

6. The apparatus of claim 1, wherein the first and second measurements are measurements of the percentage of light transmitted through the first and second samples, respectively.

7. The apparatus of claim 6, wherein the selected wavelength is 293 nanometers.

8. The apparatus of claim 1, wherein the valve system comprises first and second valves.

9. The apparatus of claim 1, wherein the single container is a cuvette.

10. The apparatus of claim 1 wherein said step of determining comprises determining the difference between the first and second measurements.

11. The apparatus of claim 1 wherein the spectral analyzer comprises a UV detector.

* * * * *